(12) United States Patent
Wiese

(10) Patent No.: US 8,065,906 B2
(45) Date of Patent: Nov. 29, 2011

(54) DETECTION OF FREE CHLORINE IN WATER

(75) Inventor: Patrick M. Wiese, Loveland, CO (US)

(73) Assignee: Hach Company, Loveland, CO (US)

( * ) Notice: Subject to any disclaimer, the term of this patent is extended or adjusted under 35 U.S.C. 154(b) by 196 days.

(21) Appl. No.: 12/487,601

(22) Filed: Jun. 18, 2009

(65) Prior Publication Data

US 2009/0320570 A1 Dec. 31, 2009

Related U.S. Application Data

(60) Provisional application No. 61/073,450, filed on Jun. 18, 2008.

(51) Int. Cl.
*G01N 37/00* (2006.01)
*C02F 1/76* (2006.01)
*C02F 1/68* (2006.01)
*G01N 33/00* (2006.01)

(52) U.S. Cl. ....... 73/61.43; 210/749; 210/754; 210/756; 210/764; 210/765; 436/111; 436/113; 436/125; 422/68.1

(58) Field of Classification Search .......... None
See application file for complete search history.

(56) References Cited

U.S. PATENT DOCUMENTS

| | | | | |
|---|---|---|---|---|
| 5,972,713 A | | 10/1999 | Kuzuhara et al. | |
| 6,315,950 B1 * | | 11/2001 | Harp et al. | 422/28 |
| 2001/0052503 A1 * | | 12/2001 | DeLonge et al. | 210/749 |
| 2003/0209498 A1 * | | 11/2003 | Baker et al. | 210/670 |
| 2003/0232447 A1 * | | 12/2003 | Kahle | 436/113 |
| 2007/0193958 A1 * | | 8/2007 | Martin | 210/749 |

OTHER PUBLICATIONS

Water Research Foundation, "Research Applications: Research in Use" Aug. 1999, pp. 1-4, online: http://www.waterresearchfoundation.org/research/TopicsAndProjects/Resources/caseStudies/researchappsChloram.aspx.
International Search Report for PCT/US09/47859, International Searching Authority, Aug. 7, 2009, pp. 1-12.
White, "Handbook of Chlorination," Van Nostrand/Reinhold, 3rd Ed., New York, pp. 589-606 (1993).
Yoon and Jensen, "Chlorine Transfer from Inorganic Monochloramine in Chlorinated Wastewater," Water Environ. Res., vol. 67, No. 5, 1995.
Isaac and Morris, "Transfer of Active Chlorine from Chloramine to Nitrogenous Organic Compounds," Environ. Sci. Technol. 17, 1983.

* cited by examiner

*Primary Examiner* — Brian J Sines
*Assistant Examiner* — Jennifer Wecker
(74) *Attorney, Agent, or Firm* — Samuel M. Freund; Cochran Freund & Young LLC

(57) ABSTRACT

The present invention describes methods and kits for determining the concentration of free chlorine in water. To avoid false readings from other species present in the water, the free chlorine is reacted with ammonia to form monochloramine, which is then reacted to form an indophenol or an indonaphthol. The concentration of the indophenol or indonaphthol is proportional to the total monochloramine present. Subtracting the concentration of residual monochloramine from the total monochloramine yields the concentration of monochloramine formed from the free chlorine and ammonia, and is proportional to the concentration of free chlorine. Embodiments of the present invention will simplify and accelerate accurate measurements of free chlorine in water, without interference from compounds impacting present measurements of free chlorine.

20 Claims, 2 Drawing Sheets

DETECTION OF FREE CHLORINE IN WATER

CROSS REFERENCE TO RELATED APPLICATIONS

This patent application claims the benefit of U.S. Provisional Patent Application No. 61/073,450 for "Detection Of Free Chlorine" by Patrick M. Wiese which was filed on 18 Jun. 2008, the entire contents of which are hereby incorporated by reference herein for all it discloses and teaches.

FIELD OF INVENTION

The invention relates to the detection of free chlorine in water. In some embodiments, this invention relates to accurately determining the concentration of free chlorine in chlorinated water, without interference from other species also present in the water.

BACKGROUND OF THE INVENTION

Accurate free chlorine determinations are important to many industries and water types. It is a required reporting parameter for many regulating agencies such as EPA and FDA. Free chlorine is considered the most effective form of chlorine disinfection in applications such as drinking water production, reuse water applications, food and poultry processing operations, and in general water use where microbial protection is required. The over-estimation of free chlorine concentrations impacts the level of actual disinfection capacity available. It is well documented in analytical methods approved for reporting free chlorine concentrations that false high concentration levels of free chlorine may be obtained when interfering substances are present.

Traditionally, treated domestic wastewater is disinfected by the addition of chlorine. More recently, many drinking water facilities have converted to chloramination to disinfect potable water. Chlorine reacts quickly with ammonia (present or added) and any organic nitrogen present in the water to form monochloramine, dichloramine (from ammonia) and organic chloramines (from organic nitrogen compounds). The relative amounts of mono-, di- and organic chloramines formed during the chloramination process depend on the ratio of chlorine-to-nitrogen, pH, temperature, mixing efficiency, and time of contact. Monochloramine and dichloramine (inorganic chloramines) are very effective biocides, but organic chloramines, as a class, have poor disinfection properties.

Monochloramine is the preferred disinfectant for most wastewater treatment facilities that employ biological-oxidation treatment processes (known as secondary treatment). Prior to disinfection, most secondary treatment plants will contain ammonia levels to between 0.5 and 10 mg/L (as nitrogen, N). At pH values between 7 and 8, and when the mass ratio of chlorine to ammonia-nitrogen is 5:1 or less, all chlorine added is converted to monochloramine. When the applied chlorine (as $Cl_2$) to ammonia-N ratio exceeds 5:1 by mass, dichloramine is formed with a corresponding drop in the total biocide concentration (monochloramine+dichloramine, expressed as $Cl_2$). Adding additional chlorine to the water eventually consumes all of the ammonia present, and a free chlorine residual emerges usually beyond a $Cl_2$:N ratio of about 9:1 by mass. This phenomenon is known as breakpoint chlorination and is depicted in FIG. 1.

Although a superior disinfectant, dichloramine formation is usually avoided since chlorine is unnecessarily consumed which results in a corresponding decrease in total oxidant concentration. Also, the presence of dichloramine can lead to pungent odors in the chlorine contact chambers of some secondary treatment facilities. Dichloramine is not desirable in potable water since its presence can affect both taste and odor.

According to White, "Handbook of Chlorination", Van Nostrand/Reinhold, 3rd Ed., New York, pp. 589-606 (1993), secondary biological wastewater treatment can produce soluble organic nitrogen concentrations in the range of 3-15 mg/L (as N). It is also stated that if the mixing of chlorine (either gaseous or liquid soda bleach) with the wastewater is poor, the chlorinated species will tend to divide between monochloramine and organic chloramines. Several studies have shown that organic chloramines have significantly less germicidal activity than monochloramine.

Studies by Yoon and Jensen, Water Environ. Res. 67, 842 (1995) and Isaac and Morris, Environ. Sci. Technol. 17, 739 (1983), have indicated that, with time, monochloramine can transfer its chlorine to nitrogenous organics, producing weaker disinfecting organic chloramines. Thus, the germicidal efficiency of chlorinated wastewater has a tendency to decrease with time.

Adequacy of disinfection may be achieved by maintaining a total oxidant residual. One way to control chlorination is by monitoring the total chlorine residual, known as Chlorine Control by Residual (CCR). In the CCR process, analytical measurements are made either manually (for example, laboratory or field testing) or automatically (for example, a process analyzer). All of the commonly used methods of analyses for CCR are based on classical iodometric chemistry. Iodide, added as a reagent, is oxidized by monochloramine, dichloramine and most organic chloramines to the tri-iodide ion:

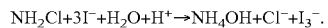

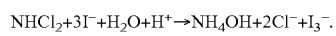

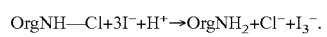

In the foregoing reactions, $NH_2Cl$ represents monochloramine, $I_3^-$ represents tri-iodide ion, $NHCl_2$ represents dichloramine, and OrgNH—Cl represents organic chloramines. The resulting tri-iodide, which is formed in direct proportion to the amount of oxidant present, is measured in several ways:

1. Colorimetrically

An indicator, such as N,N diethyl-p-phenylenediamine (DPD) is added and the tri-iodide oxidizes the indicator to a colored form, which can be measured by visual comparison, or suitable instrumentation (e.g., photometer, colorimeter or spectrophotometer). A variation of this procedure is colorimetric titration, in which after reaction of the tri-iodide with DPD, the colored product is titrated against a redox titrant, such as ferrous ammonium sulfate, to a colorless end-point.

2. Amperometrically

The tri-iodide ion may be measured using an amperometric system, consisting of a probe or cell containing dual platinum electrodes or two dissimilar electrodes (e.g., silver/platinum) and a voltage generator. A small voltage is applied across the electrodes and the resulting current is compared to a standard reference potential. A variation of this technique is amperometric titration in which the generated tri-iodide is reacted with a standard reducing titrant, such as phenylarsine oxide or sodium thiosulfate. The current decreases with decreasing concentration of tri-iodide until no tri-iodide remains, the end-point being signaled when the current no longer changes. Another variation is known as the back-titration method, in which the released tri-iodide is reacted with a known excess amount of a reductant, such as phenylarsine oxide or sodium thiosulfate. The remaining reductant is titrated with standard iodate-iodide reagent, the end-point being determined amperometrically or visually using the starch-iodide end-point.

3. Direct Titration with Visual Indication

The generated tri-iodide is titrated against standard thiosulfate titrant to a visual starch-iodide end-point.

The iodometric methods currently used for CCR are not specific for the preferred disinfectant, monochloramine. The CCR-iodometric process may overestimate the disinfection efficiency due to the presence of the poorer-disinfecting organic chloramines. Organic chloramines will be present in chlorinated wastewater due to poor mixing, chlorine transfer, or nitrification (which is explained below). Organic chloramines interfere with all of the common methods used for CCR.

Under certain circumstances, nitrification may occur in secondary-treated wastewater, where the ammonia in the wastewater is partially oxidized to nitrite. With low ammonia levels, chlorination of nitrified waters may result in direct chlorination of any organic amines present, thereby decreasing the monochloramine disinfectant level in the chlorinated water and increasing the organic chloramine level therein. Conventional CCR processes may indicate an adequate disinfection level, when, in fact, disinfection efficiency has diminished.

A second process of controlling chlorination is by use of Oxidation-Reduction Potential (ORP). ORP is based on the concept that it is the oxidative potential derived from the residual that kills the microorganisms and not the concentration of the residual. Instead of maintaining a residual, ORP chlorination control maintains a certain ORP value, measured in millivolts. FIG. 2 shows typical ORP values for different concentrations of monochloramine, dichloramine and a mixture of three organic chloramines. The organic chloramine mixture includes N-chloro-butylamine, N-chloro-diethylamine and a chlorinated tri-peptide of alanine, which is representative of organic chloramines found in chlorinated wastewater effluents.

As shown in FIG. 2, ORP can be used to distinguish between pure solutions of dichloramine and monochloramine, but cannot distinguish between monochloramine and any organic chloramines present. Therefore, the weaker disinfecting organic chloramines will also affect ORP chlorination control.

Some wastewater facilities using chlorination have difficulty meeting microbial limitations although residual testing (CCR) indicates the disinfectant concentration should be sufficient. Likewise, facilities that depend on ORP for chlorination control may experience difficulty in meeting effluent limits for disinfection, although ORP values indicate sufficient oxidation potential.

Common contaminants, including iron, manganese, hydrogen sulfide, nitrate, nitrite, ammonia, monochloramine, dichloramine, organic nitrogen, and total organic carbon, have been reported to consume free chlorine and produce false free chlorine readings based on conventional measurements. See Spon, Opflow, (June 2008) pp. 24-27. In one example, a water sample required 2.323 mg/L to satisfy the total chlorine demand. That amount is significant, considering a mandated maximum residual disinfectant level of 4.0 mg/L in public drinking water. See id. at 27. The total chlorine demand and the maximum residual disinfectant level generate a narrow window for disinfecting water, and inaccurate free chlorine readings complicate such efforts.

U.S. Pat. No. 6,315,950 B1 to Harp et al. discloses methods for disinfecting water employing monochloramine. The concentration of monochloramine is measured by reacting the monochloramine with a phenol or naphthol to form an indophenol or indonaphthol that can be detected. The '950 patent is incorporated herein by reference in its entirety.

SUMMARY OF THE INVENTION

Embodiments of the present invention provide a method for determining the concentration of free chlorine in water, including reacting the free chlorine in a sample of the water with ammonia to form monochloramine, and determining the concentration of monochloramine so formed, from which the concentration of the free chlorine in the water is determined. By converting the free chlorine to monochloramine, interferences problematic to the analysis of free chlorine concentrations in the presence of inorganic chloramines such as monochloramine and dichloramine, organochloramines, manganese, chromium and other oxidants may be eliminated or diminished which prevents or reduces the over-estimation of free chlorine concentration values, respectively.

Further embodiments of the invention provide a method for determining the concentration of free chlorine in water, including:
  determining the concentration of residual monochloramine in the water;
  reacting the free chlorine in a sample of the water with ammonia to yield formed monochloramine having a concentration which together with the concentration of residual monochloramine represents the concentration of total monochloramine in the sample;
  determining the concentration of total monochloramine in the sample; and
  subtracting the concentration of residual monochloramine from the concentration of total monochloramine to obtain the concentration of formed monochloramine, from which the concentration of free chlorine in the water is determined.

Other embodiments provide a method for determining the concentration of free chlorine in water, including:
  in a first sample of the water, determining the concentration of residual monochloramine;
  in a second sample of the water, reacting the free chlorine with ammonia to yield formed monochloramine which together with residual monochloramine represents total monochloramine;
  reacting the total monochloramine with at least one phenol, or at least one naphthol, or a combination thereof to form at least one indophenol, or the at least one indonaphthol, or a combination thereof;
  determining the concentration of the at least one indophenol, or the at least one indonaphthol, or the combination thereof, to obtain the concentration of the total monochloramine; and
  subtracting the concentration of the residual monochloramine from the concentration of the total monochloramine to obtain the concentration of the formed monochloramine, from which the concentration of the free chlorine in the water is determined.

Additional embodiments provide a method for determining the concentration of free chlorine in water, including:
  in a first sample of the water, obtaining a first signal that is proportional to the concentration of residual monochloramine in the water;
  in a second sample of the water, reacting the free chlorine to yield formed monochloramine, which together with the residual monochloramine represents total monochloramine in the second sample;

obtaining a second signal that is proportional to the concentration of total monochloramine in the second sample; and subtracting the first signal from the second signal, thereby detecting the concentration of formed monochloramine in the second sample, from which the concentration of free chlorine in the water is determined.

Still another embodiment of the present invention relates to a kit for determining the concentration of free chlorine in water, including:

a residual monochloramine portion including: at least one phenol, or at least one naphthol, or a combination thereof, in an amount effective for determining the concentration of residual monochloramine in a first sample of the water; and a total monochloramine portion including: at least one buffering agent in an amount effective for buffering a second sample of the water at a chosen pH;

ammonia in an amount effective for converting all of the free chlorine present in the second sample to monochloramine;

at least one phenol, or at least one naphthol, or a combination thereof, in an amount effective for determining the concentration of total monochloramine in the second sample of the water.

An additional embodiment relates to a kit for determining the concentration of free chlorine in water, including:

ammonia in an amount effective for converting all of the free chlorine present in a sample of the water to monochloramine;

at least one phenol, or at least one naphthol, or a combination thereof, in an amount effective for determining the concentration of total monochloramine in the sample of the water, from which the concentration of free chlorine in the water is determined.

DETAILED DESCRIPTION

Figure 1:
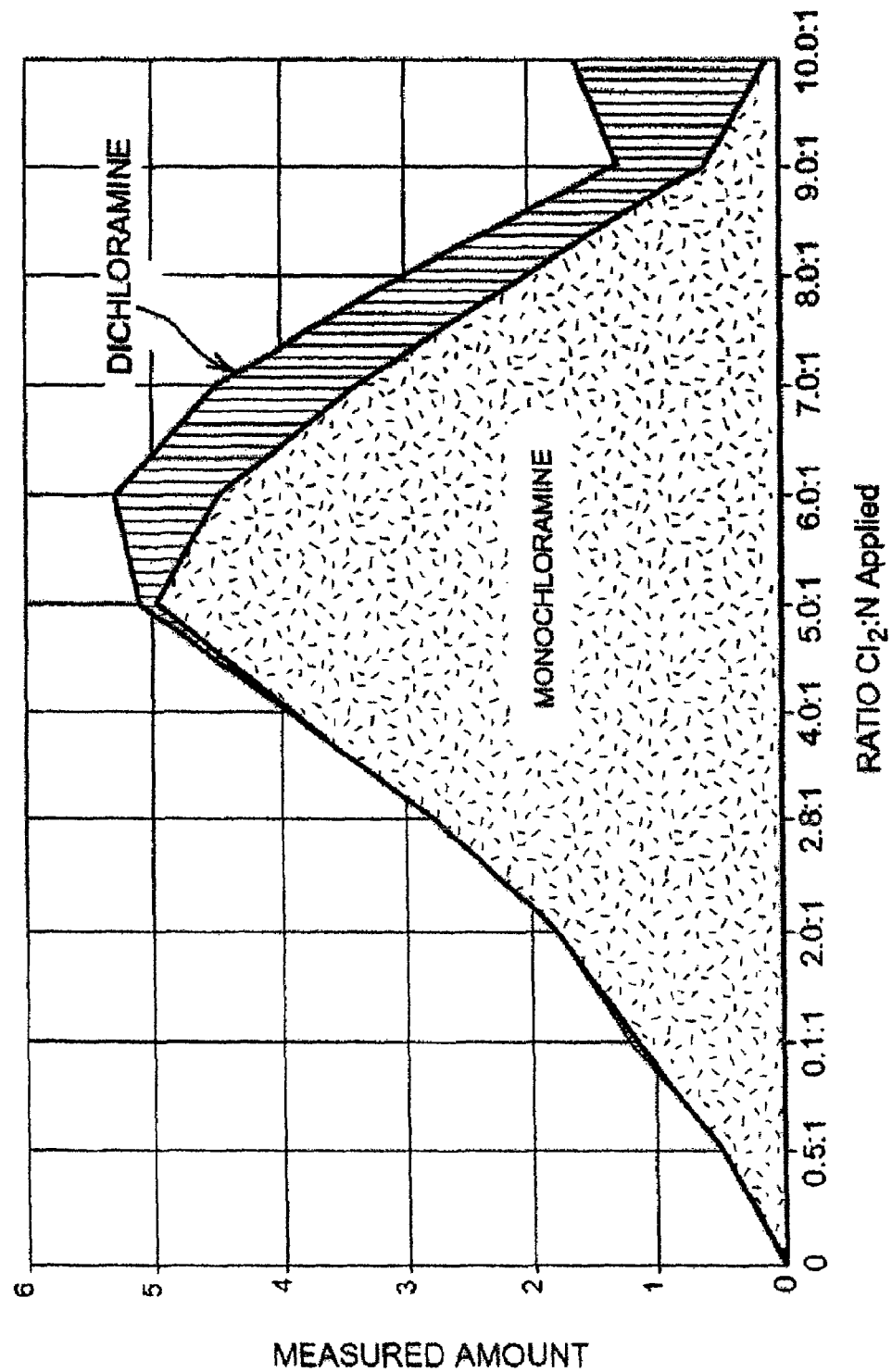
FIG. 1 is a graph illustrating the chlorination breakpoint.
Figure 2:
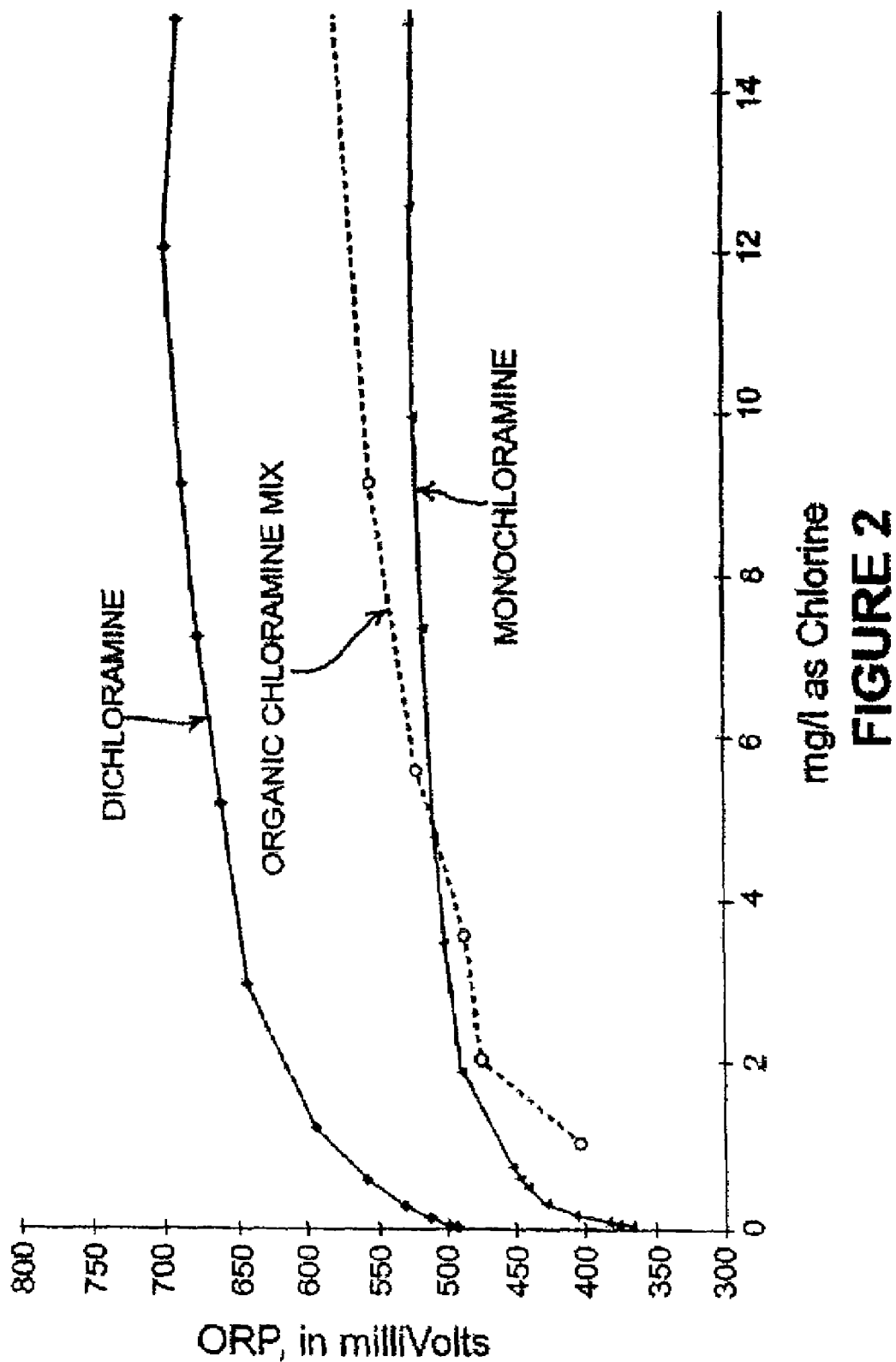
FIG. 2 is a graph illustrating ORP profiles.

The water which may contain free chlorine may be rain water, ground water, drinking water, industrial process water, industrial effluent, pool water, sewage, sludge, grey water, spring water, aquifer water, sea water, tap water, irrigation water, agricultural feed water, glacial melt water, treated water, untreated water, steam or atmospheric humidity, and virtually any other sample containing $H_2O$ for which it is desired to know the concentration of free chlorine can be tested. The water to be tested can be originally in any form, including solid, liquid, gas, or plasma.

In some embodiments, the following reactions are employed to determine the concentration of free chlorine in water.

Monochloramine Formation:

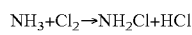

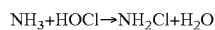

Benzoquinone Monoimine Formation:

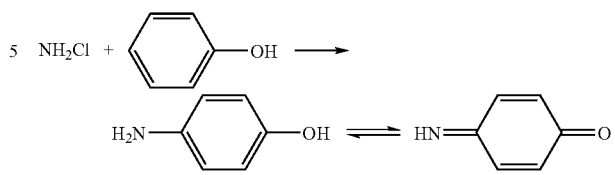

Indophenol Formation:

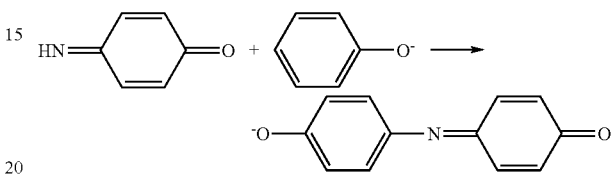

Ammonia may be added to a sample of the water to be tested to react with the free chlorine therein. The added ammonia may be in a molar amount equal to or greater than the molar amount of the free chlorine present in the sample, to ensure that all of the free chlorine reacts with ammonia. A buffering agent may also be added to the sample, before, while, and/or after adding ammonia. The sample is optionally mixed, using any suitable method, upon addition of one or more ingredients. Mixing may include stirring, shaking and inverting the sample, as examples. At least one ionic strength adjuster may be added to the sample, before, while, and/or after adding the ammonia.

Samples may be buffered at a chosen pH. The pH of different samples may be adjusted and buffered to be different or the same. In certain embodiments, the pH may be chosen to be between about 2 and about 12. In other embodiments, the pH may be chosen to be between about 7.0 and about 9.5. In still other embodiments, the pH may be chosen to be about 8.3. Buffering may be accomplished by the addition of an effective buffering agent or agents, which may include, but are not limited to, imidazole, tris(hydroxymethyl)aminomethane, morpholine, triethanolamine, bicine, one or more conjugate acids of any of the foregoing, one or more conjugate bases of any of the foregoing, one or more inorganic salts of phosphate, one or more inorganic salts of pyrophosphate, one or more inorganic salts of borate, one or more inorganic salts of hydroxide, and combinations of two or more of any of the foregoing. Thus, as an example, morpholine, morpholine HCl, lithium hydroxide, and trisodium borate can be used to buffer a sample. Buffering agents may include disodium potassium borate or calcium hydrogen borate, or one or more tri-alkali salts of borate, such as trilithium borate, trisodium borate, tripotassium borate, and combinations thereof, such as dilithium potassium borate, as examples.

A compound and one or more of its salts may be added to a sample to form a buffer at a desired pH, the compound and its salts both being buffering agents. For example, borate and trisodium borate may be added in a certain molar ratio to buffer the sample of water at a given pH. Those of ordinary skill in the art can readily determine such molar ratios based on the desired pH, the relevant equilibrium constants, and other factors, or upon facile experimentation.

At least one ionic strength adjuster may be added to a sample of water, and may include, but are not limited to, one or more sodium salts of citrate, one or more potassium salts of citrate, one or more sodium salts of tartrate, one or more potassium salts of tartrate, sodium acetate, potassium acetate, one or more sodium salts of succinate, one or more potassium salts of succinate, and combinations of two or more of the foregoing. As examples, one or more sodium salts of citrate includes, but is not limited to, monosodium citrate, disodium citrate, trisodium citrate, monosodium monopotassium citrate, and the like. The latter is both a sodium salt and a potassium salt of citrate since it contains at least one sodium ion, and it contains at least one potassium ion.

At least one ionic strength adjuster may be added in an amount sufficient to adjust the ionic strength to between about 0.01 M and about 10 M. In other embodiments, the at least one ionic strength adjuster is added in an amount effective for adjusting the ionic strength to between about 0.1 M and about 1 M.

Aqueous ammonia, ammonia gas, and one or more ammonium salts are effective for some embodiments of the present invention. When the reagents are to be stored in powder form, ammonium salts may be used, and the amount of buffering agent(s) may be adjusted to ensure the desired pH. Optionally, a base or an acid may be employed in additional embodiments of the invention to assist the buffering agent(s).

The at least one phenol, or the at least one naphthol, or the combination thereof may include one or more of any effective phenol and/or naphthol, and phenols substituted with at least one substituent, such as an ortho-substitution which may lower the susceptibility of the phenol ring to nucleophilic attack. Substituted alpha naphthols, including ortho-substituted naphthols, may also be used. The at least one phenol, the at least one naphthol, or the combination thereof may include one or more of sodium salicylate, salicylic acid, 2-hydroxybenzyl alcohol, 3-hydroxybenzyl alcohol, alpha-naphthol, 1-naphthol-2-sulfonic acid, 1-hydroxy-2-naphthoic acid, salicylaldehyde, 2-hydroxy acetophenone, 2-methoxyphenol, o-chlorophenol, and o-cresol.

The reaction between monochloramine (residual or formed) and the at least one phenol, or the at least one naphthol, or the combination thereof may proceed in the presence of at least one catalyst, such as nitroprussides, alkali metal salts of nitroferricyanide: sodium nitroferricyanide, potassium nitroferricyanide, or both, being examples. The at least one catalyst may be added at 5% or less by weight of the reagents used to form the indophenol, or the indonaphthol, or the combination thereof. In one example, the catalyst may be added in a chosen ratio with the at least one phenol, the at least one naphthol, or a combination thereof of about 1:10 by weight.

A series of colored panels may be used for calorimetric comparison by eye; while other embodiments provide calorimetric comparison with an instrument such as, for example, a calorimeter, photometer, or spectrophotometer. Sample absorbance may be measured at wavelengths of light between about 600 nm and about 800 nm, the region where indophenol and indonaphthol absorb. In other embodiments, amperometric analysis may be employed, wherein the indophenol, indonaphthol, or combination thereof, is oxidized or reduced, and the resulting current is a measure of the concentration.

Residual monochloramine concentration may be measured calorimetrically, amperometrically, or by titration and visual indication. In certain embodiments, the residual monochloramine concentration is determined by reacting the residual monochloramine with at least one phenol, or at least one naphthol, or a combination thereof to form at least one indophenol, or at least one indonaphthol, or a combination thereof, respectively; and determining the concentration of the at least one indophenol, or at least one indonaphthol, or the combination thereof, to obtain the concentration of the residual monochloramine. As described herein, reacting the residual monochloramine with at least one phenol, or at least one naphthol, or combination thereof may proceed in the presence of at least one catalyst. Suitable catalysts include, for example, alkali metal salts of nitroferricyanide.

Determining the concentration of residual monochloramine may rely on an assumption based, for example, upon historical data. Accordingly, it may be assumed that the water being tested contains substantially the same residual monochloramine as it historically had. "Historically" may mean any suitable length of time, including but not limited to hourly, daily, weekly, monthly, and yearly. The historical concentration of residual monochloramine is subtracted from the measured concentration of total monochloramine, to obtain the concentration of formed monochloramine, from which the concentration of free chlorine in the water is determined.

Further embodiments of the present invention involve the determination of free ammonia in the water. Knowledge of the free ammonia and the free chlorine concentrations for a given water sample may assist with determining where the water sample resides on the breakpoint chlorination curve (see FIG. 1). A significant free ammonia concentration indicates relatively little chlorination, likely less than 5:1 $Cl_2$:N by mass. Free ammonia may be converted to monochloramine by adding additional free chlorine under controlled pH and alkalinity conditions and determined as monochloramine using the indophenol method described in U.S. Pat. No. 6,315,950 B1. Alternatively, the free ammonia can be determined using an ion selective electrode specific for ammonia. See, for example, U.S. Pat. No. 5,198,092.

The steps of the methods of various embodiments of the present invention, unless logic or explicit language indicates otherwise, can be performed in any effective order. Most reactants can be mixed together simultaneously, sequentially, or combinations thereof. In some embodiments, a reaction may be allowed to continue for about 10 s before the next step, for example, another reaction being started, another ingredient being introduced, and/or a reading being taken. Reactions may be permitted to continue for between about 20 s, and about 1 h.

Reactions may occur at temperatures between about 0° C. and about 100° C. Reactions may also occur at temperatures between about 5° C. and about 50° C., between about 10° C. and about 40° C., between about 15° C. and about 30° C., or from between 18° C. and about 25° C. Yet other embodiments allow reactions to occur substantially at ambient temperature. Still other embodiments allow reactions to occur without temperature control, and the temperature rises or falls to a level determined by the ambient conditions and the thermodynamics of the reactions taking place, among other factors. In certain embodiments, a reaction occurring without temperature control occurs substantially at ambient temperature.

Additional embodiments provide the reactions at greater than or less than ambient pressure, with such pressures controlled by any effective means, such as vacuum pumps, gas compressors, and the like, as desired.

Kits resembling conventional water-testing kits, with a vessel for obtaining a sample of the water to be tested, and one or more compositions for adding testing reagents to the sample may be used to determine the concentration of free chlorine in a water sample. Optionally, the vessel may be graduated to indicate the volume of the sample. In other embodiments, the kit comprises a color panel to allow for visual color comparison, thereby indicating the concentration of indophenol, indonaphthol, or a combination thereof.

Kits may include one or more reactants for determining free chlorine concentration, such as ammonia and at least one buffering agent for the total monochloramine measurement. In another embodiment, a kit for total monochloramine measurement may include one or more compositions comprising ammonia; at least one buffering agent; at least one phenol, or at least one naphthol, or a combination thereof; and at least one catalyst. In still another embodiment for a residual monochloramine measurement, a kit may include at least one phenol, or at least one naphthol, or a combination thereof; and at least one catalyst. A kit may optionally include instructions for adding and mixing the composition(s) with the sample and for determining the concentrations to be sought.

Compositions providing the reagents for the kits can be in any suitable form: solid, liquid, and gases being possible. Some embodiments may provide at least one liquid composition in a deformable container that forms drops of fairly consistent volume when inverted, thereby delivering a consistent amount of composition to a sample. Other embodiments provide at least one solid composition, either in loose form (powder, granules, or pellets) or in a dosage form such as a tablet or capsule. A tablet or capsule may include one or more dissolution aids, such as, for example, salts and other water-soluble adjuvants, and one or more binders. Liquids may comprise an effective solvent, such as, for example, one or more of water, lower alcohols, other polar solvents, and the like, solvents being at least partially miscible with water such that reagents are efficiently transferred.

In additional embodiments of the invention, kits may provide what is necessary to carry out the methods of the present invention described herein. For example, a kit may include at least one buffering agent in an amount sufficient to buffer a first sample of water at the pH at which a second sample is buffered. A kit may include at least one ionic strength adjuster in an amount sufficient to adjust the ionic strength of the water sample. A portion of a kit (for example, for measuring residual monochloramine or total monochloramine, or both) may include at least one catalyst in an amount sufficient to catalyze the formation of at least one monoimine in the water sample. At least one portion of the kit may include a buffering agent in an amount sufficient to buffer the water sample at a pH between about 2 and about 12; from between 7.0 and about 9.5; or about 8.3. Kits according to the present invention may include a portion for determining the concentration of free ammonia in the water.

In some embodiments, the chemistry used to determine the residual monochloramine and the total monochloramine portion may be different, while in other embodiments, it may be the same. For example, in one embodiment, the at least one phenol, or the at least one naphthol, or the combination thereof for one measurement differs from the at least one phenol, or the at least one naphthol, or the combination thereof in another measurement. In another embodiment, the at least one phenol, or the at least one naphthol, or the combination thereof is the same in both portions. In another embodiment, the chemistry used to determine the concentration of residual monochloramine may not employ at least one phenol, or the at least one naphthol, or a combination thereof, but uses some other technique such as known by those skilled in the art.

Where the same chemistry is used to determine both the residual monochloramine concentration and the total monochloramine concentration, an instrument, such as a calorimeter, a photometer, or a spectrophotometer, as examples, may be employed. In such situations, the concentration of formed monochloramine may be determined by subtracting the signal from the residual monochloramine measurement from the total monochloramine measurement to give a signal proportional to the concentration of formed monochloramine, from which the concentration of free chlorine can be determined. Accordingly, the present invention also provides a method for determining the concentration of free chlorine in water comprising:

in a first sample of the water, reacting residual monochloramine with at least one phenol, at least one naphthol, or a combination thereof, optionally in the presence of at least one catalyst, to form at least one indophenol, at least one indonaphthol, or a combination thereof;

obtaining a first signal from the first sample that represents the concentration of the at least one indophenol, at least one indonaphthol, or the combination thereof, and thereby indicates the concentration of residual monochloramine in the first sample;

in a second sample of the water, reacting free chlorine with ammonia to yield formed monochloramine, optionally in the presence of at least one buffering agent to buffer the second sample to a pH;

reacting the formed monochloramine and residual monochloramine in the second sample with the at least one phenol, at least one naphthol, or the combination thereof reacted in the first sample, in the presence of the at least one catalyst if present in the first sample, to form the at least one phenol, at least one naphthol, or the combination thereof in the second sample;

obtaining a second signal from the at least one sample that represents the concentration of the at least one indophenol, at least one indonaphthol, or the combination thereof, and thereby indicates the concentration of total monochloramine in the second sample;

subtracting the first signal from the second signal to determine the concentration of formed monochloramine from which the concentration of free chlorine in the water sample is determined.

The signal from the first sample may be used as a blank or reference for an instrument, wherein instrument may automatically subtract the signal from the first sample, thereby providing data proportional to the concentration of free chlorine in the water. The signals obtained from the first and second samples can be any suitable signals, whether optical, electrical, electromagnetic, electrochemical, electromechanical, digital, analogue, or otherwise. Those signals can be generated by any suitable instrument, including but not limited to spectrometers, electrochemical cells, and the like.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:
1. A method for determining the molar amount of free chlorine in water, comprising:
reacting the free chlorine in a sample of the water with ammonia in an amount equal to or greater than the molar amount of free chlorine to form monochloramine; and determining the concentration of monochloramine so formed, from which the concentration of the free chlorine in the water is determined.

2. A method for determining the molar amount of free chlorine in water, comprising:
   determining the concentration of residual monochloramine in the water;
   reacting the free chlorine in a sample of the water with ammonia in an amount equal to or greater than the molar amount of free chlorine to yield formed monochloramine having a concentration which together with the concentration of residual monochloramine represents the concentration of total monochloramine in the sample;
   determining the concentration of total monochloramine in the sample; and
   subtracting the concentration of residual monochloramine from the concentration of total monochloramine to obtain the concentration of formed monochloramine, from which the concentration of free chlorine in the water is determined.

3. A method for determining the molar amount of free chlorine in water, comprising:
   in a first sample of the water, determining the concentration of residual monochloramine;
   in a second sample of the water, reacting the free chlorine with ammonia in an amount equal to or greater than the molar amount of free chlorine to yield formed monochloramine which together with residual monochloramine represents total monochloramine;
   reacting the total monochloramine with at least one phenol, or at least one naphthol, or a combination thereof to form at least one indophenol, or at least one indonaphthol, or a combination thereof;
   determining the concentration of the at least one indophenol, or the at least one indonaphthol, or the combination thereof, to obtain the concentration of the total monochloramine; and
   subtracting the concentration of the residual monochloramine from the concentration of the total monochloramine to obtain the concentration of the formed monochloramine from which the concentration of the free chlorine in the water is determined.

4. The method of claim 3, further comprising the step of buffering the second sample at a chosen pH.

5. The method of claim 4, wherein the chosen pH is between about 2 and about 12.

6. The method of claim 4, wherein the chosen pH is between about 7.0 and about 9.5.

7. The method of claim 4, wherein the chosen pH is about 8.3.

8. The method of claim 4, wherein said step of buffering comprises adding to the second sample at least one buffering agent chosen from imidazole, tris(hydroxymethyl)aminomethane, morpholine, triethanolamine, bicine, one or more conjugate acids of any of the foregoing, one or more conjugate bases of any of the foregoing, one or more inorganic salts of phosphate, one or more inorganic salts of pyrophosphate, one or more inorganic salts of borate, and combinations of two or more of any of the foregoing.

9. The method of claim 4, wherein said step of buffering comprises adding at least one buffering agent chosen from one or more inorganic salts of borate to the second sample.

10. The method of claim 3, further comprising the step of adding at least one catalyst to the second sample.

11. The method of claim 10, wherein the at least one catalyst comprises at least one salt of nitroferricyanide.

12. The method of claim 11, wherein the at least one salt of nitroferricyanide comprises sodium nitroferricyanide.

13. The method of claim 3, further comprising the step of adding at least one ionic strength adjuster to the second sample.

14. The method of claim 13, wherein the at least one ionic strength adjuster is chosen from one or more sodium salts of citrate, one or more potassium salts of citrate, one or more sodium salts of tartrate, one or more potassium salts of tartrate, sodium acetate, potassium acetate, one or more sodium salts of succinate, one or more potassium salts of succinate, and combinations of two or more of the foregoing.

15. The method of claim 3, wherein the at least one phenol, or the at least one indonaphthol, or the combination thereof is ortho-substituted.

16. The method of claim 3, wherein the at least one phenol, or the at least one naphthol, or the combination thereof is chosen from one or more of sodium salicylate, salicylic acid, 2-hydroxybenzyl alcohol, 3-hydroxybenzyl alcohol, alpha-naphthol, 1-naphthol-2-sulfonic acid, and 1-hydroxy-2-naphthoic acid.

17. The method of claim 1, further comprising the step of determining the concentration of free ammonia in the water.

18. The method of claim 2, further comprising the step of determining the concentration of free ammonia in the water.

19. The method of claim 3, further comprising the step of determining the concentration of free ammonia in the water.

20. A method for determining the molar amount of free chlorine in water, comprising:
   in a first sample of the water, obtaining a first signal that is proportional to the concentration of residual monochloramine in the water;
   in a second sample of the water, reacting the free chlorine with a molar amount of nitrogen greater than or equal to the molar amount of free chlorine to yield formed monochloramine, which together with residual monochloramine represents total monochloramine in the second sample;
   obtaining a second signal that is proportional to the concentration of total monochloramine in the second sample; and
   subtracting the first signal from the second signal, thereby detecting the concentration of formed monochloramine in the second sample, from which the concentration of free chlorine in the water is determined.

* * * * *